(12) United States Patent
Steenkamp et al.

(10) Patent No.: US 9,434,710 B2
(45) Date of Patent: Sep. 6, 2016

(54) METHOD FOR CONVERTING ALOERESIN A TO ALOESIN

(75) Inventors: Lucia H. Steenkamp, Boksburg (ZA); Robin K. Mitra, Manchester (GB); Steven James Heggie, Parks Road (GB); Vuyisile N. Phehane, Centurion (ZA)

(73) Assignee: CSIR, BIO/CHEMTEK, Modderfontein (ZA)

(*) Notice: Subject to any disclaimer, the term of this patent is extended or adjusted under 35 U.S.C. 154(b) by 538 days.

(21) Appl. No.: 11/909,063

(22) PCT Filed: Mar. 13, 2006

(86) PCT No.: PCT/IB2006/000542
§ 371 (c)(1),
(2), (4) Date: May 13, 2008

(87) PCT Pub. No.: WO2006/097811
PCT Pub. Date: Sep. 21, 2006

(65) Prior Publication Data
US 2008/0280348 A1    Nov. 13, 2008

(30) Foreign Application Priority Data

Mar. 18, 2005 (ZA) ................. 2005/02308
Mar. 18, 2005 (ZA) ................. 2005/02310

(51) Int. Cl.
*C07D 311/22* (2006.01)
*C07D 407/04* (2006.01)

(52) U.S. Cl.
CPC ........... *C07D 311/22* (2013.01); *C07D 407/04* (2013.01)

(58) Field of Classification Search
None
See application file for complete search history.

(56) References Cited

U.S. PATENT DOCUMENTS

| 4,656,029 | A | * | 4/1987 | Grollier et al. ................. 424/47 |
| 4,735,935 | A | | 4/1988 | McAnalley |
| 4,944,953 | A | * | 7/1990 | Hartman et al. .............. 426/271 |
| 5,652,265 | A | * | 7/1997 | Vittori .................. A61K 31/122 514/548 |
| 6,451,357 | B1 | * | 9/2002 | Farrow .......................... 424/744 |

FOREIGN PATENT DOCUMENTS

| JP | 62286909 A | * | 12/1987 |
| JP | 08325155 A | * | 12/1996 |
| JP | 09241163 A | * | 9/1997 |

OTHER PUBLICATIONS

Unterberg. How to Respond to Hazardous chemical spills. Technology & Engineering. 1988. p. 197.*
Aloe Trade. Retrieved from the internet. Retrieved on Dec. 30, 2010. <http://www.aloetradeamerica.com/aloe_main_two_components_gel_and_bitter>. pp. 1-5.*
Makino et al. The Structures of the Two New Aloesin Esters. Chem Pharm Bull. vol. 22. 1974. pp. 1565-1570.*
Van Wyk et al. Geographic Variation in the Major Compounds of Aloe Ferox Leaf Exudate. Planta Medica. 1995. 61(3). pp. 250-253.*
Gramatica et al. Aloe Revisited the Structure of Aloeresin A. Tetraherdron Letters. vol. 23. No. 23. 1982 pp. 2423-2424.*
Che et al., "Metabolism of Aloesin and Related Compounds by Human Intestinal Bacteria: A Bacterial Cleavage of the C-Glucosyl Bond and the Subsequent Reduction of the Acetonyl Side Chain," *Chem. Pharm. Bull.*, 39(3):704-708 (1991).
Gramatica et al., "Aloe Revisited, The Structure of Aloeresin A," *Tetrahedron Lett.*, 23(23):2423-2424 (1982).
International Preliminary Report on Patentability for International Application No. PCT/IB2006/000542, dated Jul. 24, 2007, 7 pgs.
International Search Report for International Application No. PCT/IB2006/000542, dated Jul. 6, 2006, 2pgs.
Written Opinion for International Application No. PCT/IB2006/000542, dated Jul. 6, 2006, 2pgs.
Tetrahedron Letters, "The New Observation of Intramolecular Acyl Transfer from Aglycon to Sugar of C-Glycoside. The Regioselective and Single Step Acylation of 2'-Hydroxil Group of Free C-Glucopyranoside." 1997, vol. 38 (36), p. 6411-6414.
Giovanna Speranza et al., "Aloeresin C, a bitter c,o-diglucoside from Cape Aloe. Phytochemistry." 1985. vol. 24, Issue 7, p. 1571-1573.
McCarthy et al., "The Distribution of Aloesin in Some South African *Aloe* Species; Heft 3," 342-44 (1967).
Hanes et al., "C-Glycosyl Compounds. Part VI. Aloesin, a C-Glucosylchromone from *Aloe* sp.$^2$," *J. Chem. Soc.*, (C):2581-2586 (1970).
Holdsworth, "Chromones in *Aloe* Species, Part I—Aloesin—a C-glucosyl-7-hydroxychromone," 19(4):322-325 (1972).
Mebe, "2'-p-Methoxycoumaroylaloeresin, A C-Glucoside from *Aloe excelsa*," *Phytochemistry*, 26(9):2646-47 (1987).
Conner et al., "Anthrone and Chromone Components of *Aloe cremnophila* and *A. jacksonII* Leaf Exudates," *Phytochemistry*, 29(3):941-44 (1990).

(Continued)

*Primary Examiner* — Amy L Clark
(74) *Attorney, Agent, or Firm* — Marshall, Gerstein & Borun LLP

(57) ABSTRACT

The invention provides a process for hydrolytically converting aloeresin A to aloesin by the following reaction: The amount of aloesin available for extraction from sap of aloe plants is thereby increased and the extraction and purification of the aloesin is also made easier and less costly. As aloesin is more commercially valuable than aloeresin A, the process also increases the commercial value of the sap or aloe bitters from the aloe plant. The process optionally also includes the step of separating the aloesin from the p-coumaric acid. Typical hydrolysis steps that are used in the process are acid hydrolysis, base hydrolysis and enzymatic hydrolysis. In the case of acid hydrolysis, the acid is any suitable organic or inorganic acid, such as hydrochloric acid, sulfuric acid, nitric acid or phosphoric acid. In the case of enzymatic hydrolysis, the hydrolytic enzyme is typically an esterase, a lipase or a protease.

5 Claims, No Drawings

(56) References Cited

OTHER PUBLICATIONS

Rauwald et al., "High-Performance Liquid Chromatographic Separation and Determination of Diastereomeric Anthrone-C-Glucosyls in Cape Aloes.," *J. of Chromatography*, 639:359-62 (1993).

Rauwald et al., "5-Hydroxyaloin A in the Genus *Aloe* Thin Layer Chromatographic Screening and High Performance Liquid Chromatographic Determination," *Z. Naturforsch*, 48c:1-4 (1993).

Grindlay et al., "The *Aloe vera* Phenomenon: A Review of the Properties and Modern Uses of the Leaf Parenchyma Gel," *J. of Ethnopharmacology*, 16:117-151 (1986).

"WHO Monographs on Selected Medicinal Plants," World Health Organization, vol. 1(1999). Retrieved from the Internet: http://apps.who.int/medicinedocs/pdf/s2200e/s2200e.pdf (295 pages) on Jun. 26, 2015.

* cited by examiner

METHOD FOR CONVERTING ALOERESIN A TO ALOESIN

CROSS-REFERENCE TO RELATED APPLICATIONS

This is the U.S. national phase application of International Application No. PCT/IB2006/000542, filed Mar. 13, 2006, which claims the benefit of South Africa patent application. No. 2005/02308, filed Mar. 18, 2005, and South Africa patent application No. 2005/02310, filed Mar. 18, 2005.

BACKGROUND OF THE INVENTION

The invention relates to a method for converting aloeresin A to aloesin.

Aloe is a succulent plant of which more than 300 species are known to exist, most of which are indigenous to Africa. Products from the aloe have been used in traditional medicine for centuries and in particular have been used in dermatological applications for the treatment of burns, sores and other wounds. Modern therapeutic observations include anti-inflammatory activity, anti-tumor activity, anti-acid activity, anti-diabetic activity, tyrosinase inhibiting activity and antioxidant activity. Aloe products are also used extensively in the cosmetic and health food industries, especially with the recent increase in popularity of natural products.

The main species of African aloe from which pharmaceutical, therapeutic, dermatological or cosmetic applications are obtained is *Aloe ferox*, a species restricted to Southern Africa. Other species of aloe are also used for similar purposes. Aloe vera is used extensively in the USA in skin care products, shampoos and health drinks. *A. ferox* has, however, been found to have several superior properties to *A. vera*. For example, *A. ferox* has a higher calcium and total amino acid content than *A. vera*. The cut leaf of cultivated *A. ferox* plants also produces approximately 20 times more bitter sap, weight for weight, than an *A. vera* plant growing beside it. Since *A. ferox* leaves are much thicker and wider, the total yield of bitter sap per leaf is even greater. The amount of gel recovered from *A. ferox* is also consistently greater in volume than that obtained from *A. vera*.

Many methods exist for the isolation of particular components of the aloe (see, for example, U.S. Pat. Nos. 4,735,935 and 4,656,029). One of the commercial products of the aloe is obtained from the sap produced by the leaf of the aloe and is called aloe bitters due to its bitter taste. The sap is collected and dried by traditional methods which will be known to persons skilled in the art to produce a dark brown solid substance known as aloe bitters or Cape Aloes.

Commercial aloe bitters contains four major constituents, i.e. aloin A, aloin B, aloesin and aloeresin A.

The overall composition of major compounds in *A. ferox* leaf exudate is remarkably invariable, especially when the morphological variation and wide natural distribution area of this species are considered. In *A. ferox*, aloeresin A, aloesin and aloin (both epimers A and B) contribute between 70% and 97% of total dry weight, in a ratio of approximately 4:3:2 respectively.

Aloin A and B (or barbaloin) are isolated from aloe bitters, normally by selective extraction, and are principally used as a purgative. Aloesin is also isolated from aloe bitters and is used as a skin lightening and sunscreen agent (U.S. Pat. No. 4,656,029). The aloeresin A is usually discarded. Thus, although aloeresin A is present in the largest quantity in the aloe sap, it has little or no commercial value. It would therefore be advantageous to convert the aloeresin A into a compound which has a higher commercial value.

In the description which follows, any reference to aloe sap is also intended to refer to aloe bitters or an extract of aloe bitters.

SUMMARY OF THE INVENTION

According to a first embodiment of the invention there is provided a method for converting aloeresin A to aloesin, the method including the step of hydrolysing at least a portion of the aloeresin A to aloesin and p-coumaric acid.

The method may further include the step of separating the aloesin from the p-coumaric acid.

The step of hydrolyzing the aloeresin A to aloesin may be performed using acid hydrolysis.

Alternatively, the step of hydrolyzing the aloeresin A to aloesin may be performed using a hydrolytic enzyme.

In the case of acid hydrolysis, the acid may be any organic or inorganic acid. In particular, the acid may be one or more acid selected from the group consisting of hydrochloric acid, sulfuric acid, nitric acid and phosphoric acid.

In the case of enzymatic hydrolysis, the hydrolytic enzyme may be an esterase, a lipase or a protease.

In particular, the hydrolytic enzyme may be selected form the group consisting of *Aspergillus oryzae* protease, ESL 00102™ from Diversa, NOVO 388™ from Nordisk, and *Mucor miehei* lipase from the ALTUS CHIROSCREEN KIT™. More particularly, the enzyme may be either AMANO PROTEASE M™ or BIOPROTEASE P CONC™ from Quest International, both being the protease from *Aspergillus oryzae*.

Alternatively, the enzyme may be an enzyme which is encoded by a DNA or amino acid sequence which at least substantially corresponds to the DNA or amino acid sequence of any one of the enzymes mentioned above or partial sequences thereof.

The DNA or amino acid sequence of the enzyme may have at least 70% homology with the DNA or amino acid sequence of the above enzymes.

The enzyme may be in either solid or liquid form.

Preferably, the aloeresin A is converted to aloesin and p-coumaric acid without the formation of by-products, and in particular, without the formation of polymers.

The aloeresin A may be obtained from any species of the aloe plant, in particular from the *A. ferox* or *A. vera* species, and more particularly, from the *A. ferox* species.

The aloeresin A may be obtained from sap produced by leaves of the aloe plant. The sap may be in liquid or solid form.

The aloeresin A may be in partially purified form.

The hydrolysis step when using an acid may be carried out in an acid concentration range of from about 0.5 N to about 10 N, and is optimally carried out at a concentration of from about 2 N to about 5 N acid.

The hydrolysis step may be carried out at from about 20 to about 121° C., and when using an acid, is typically carried out at about 90° C. When using a hydrolytic enzyme, the hydrolysis step is typically carried out at about 37° C., except when using ESL001-02™, in which case the hydrolysis step may be carried out at from about 50 to about 90° C., and more particularly at about 70° C.

A buffer may be used in the reaction medium. The buffer may be a sodium phosphate, carbonate or borate buffer or water, or any other buffer having a $pK_a$ in the pH range of from about 4 to about 8. The buffer concentration may be in the range of from 0.01 M to 1 M, and is preferably 0.1 M.

An organic solvent may be added, such as ethanol or acetone in concentrations of from about 10 to 50% and preferably at about 30%.

According to a second embodiment of the invention, there is provided a method for extracting aloesin from sap of an aloe plant, the method including the steps of:

hydrolysing at least a portion of aloeresin A in the aloe plant to aloesin and p-coumaric acid; and extracting from the sap naturally occurring aloesin and the aloesin converted from the aloeresin A.

The aloe plant may be of the *A. ferox* species. The sap may be in a liquid or solid form.

The aloeresin A may be hydrolysed according to a method substantially as described above.

According to a third embodiment of the invention there is provided aloesin formed by hydrolysing aloeresin A to aloesin and p-coumaric acid, substantially as described above.

The aloeresin A may be from sap of the aloe plant, and more particularly may be from sap of the *A. ferox* species.

The aloesin may be a combination of naturally occurring aloesin and aloesin converted from aloeresin A according to the method described above.

DETAILED DESCRIPTION OF THE INVENTION

A process for hydrolytically converting aloeresin A to aloesin is described herein.

Aloeresin A is an aloesinyl ester of p-coumaric acid, and the applicant has found that it is possible to efficiently and economically hydrolyse aloeresin A to aloesin (a C-glycoside-5-methylchromone), thereby increasing the amount of aloesin available for extraction from sap of aloe plants. As aloesin is more commercially valuable than aloeresin A, the process also increases the commercial value of the sap or aloe bitters from the aloe plant. The conversion reaction of aloeresin A to aloesin is depicted below:

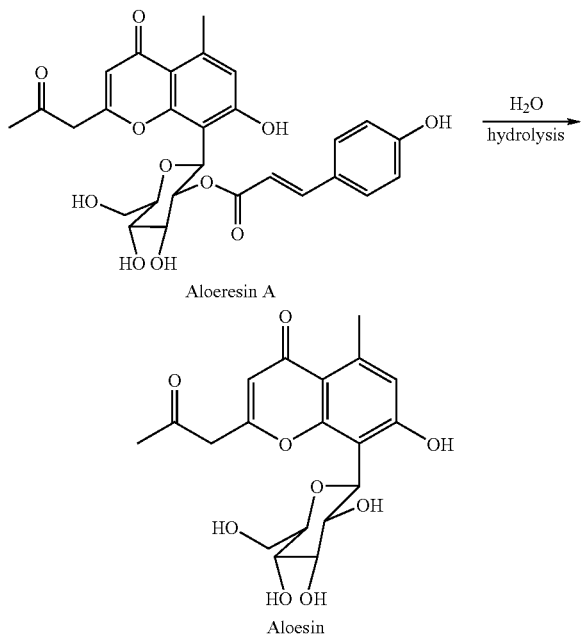

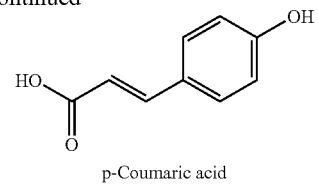

p-Coumaric acid

The conversion of aloeresin A to aloesin also facilitates the selective removal of the aloesin, as well as byproducts aloin A and B from the aloe bitters. The extraction and purification of aloesin in the absence of aloeresin A is much less difficult and costly than in the presence of aloeresin A, for two main reasons:

(a) after conversion, there is more aloesin that can be extracted; and (b) after conversion, only two main components (aloesin and aloin) need to be separated from the aloe bitters, and as these have very different physical properties, selective extraction of aloesin becomes much easier.

The process may also include the step of separating the aloesin from the p-coumaric acid. Suitable separation steps will be apparent to persons skilled in the art and will not be discussed in detail herein, although typical separation processes include solvent extraction, chromatography and crystallisation.

Examples of hydrolysis steps that can be used in the process are acid hydrolysis, base hydrolysis and enzymatic hydrolysis.

In the case of acid hydrolysis, the acid can be any organic or inorganic acid, such as hydrochloric acid, sulfuric acid, nitric acid, phosphoric acid and so forth.

In the case of enzymatic hydrolysis, the hydrolytic enzyme can be an esterase, a lipase or a protease, such as *Aspergillus oryzae* protease, ESL 001-02 ™ from Diversa, NOVO 388™ from Nordisk (particularly the protease contaminant in the preparation), or *Mucor miehei* lipase from the ALTUS CHIROSCREEN KIT™. More particularly, the enzyme is either PROTEASE M™ from Amano or BIO-PROTEASE P CONC™ from Quest International, both being the protease from *Aspergillus oryzae*. Alternatively, the enzyme could be an enzyme which is encoded by a DNA or amino acid sequence which at least substantially corresponds to the DNA or amino acid sequence of any one of the enzymes mentioned above or partial sequences thereof. The DNA or amino acid sequence of the enzyme could have at least 70% homology with the DNA or amino acid sequence of the above enzymes. The enzyme is in either solid or liquid form.

The aloeresin A is typically converted to aloesin and p-coumaric acid without the formation of by-products, such as polymers.

Any species of the aloe plant is suitable as a source of aloeresin A, which is obtainable from sap produced by leaves of the aloe plant. The sap may be in liquid or solid form, and the aloeresin A can be in purified form, in partially purified form or may be in unpurified form within the sap or another part of the aloe plant.

The hydrolysis step, when using an acid, is generally carried out in an acid concentration range of from about 0.5 N to about 10 N, and is optimally carried out at a concentration of from about 2 to about 5 N acid. An organic solvent, such as ethanol or acetone in concentrations of from about 10 to 50% and preferably at about 30%, may optionally be added to the reaction process.

The hydrolysis step is generally carried out at from about 20 to about 121° C., and when using an acid, is typically carried out at about 90° C. When using a hydrolytic enzyme, the hydrolysis step is typically carried out at about 37° C., except when using enzyme ESL001-02, in which case the hydrolysis step is carried out at from about 50 to about 90° C., and more particularly at about 70° C.

A buffer can be used in the reaction medium. The buffer may be a sodium phosphate, carbonate or borate buffer or water, or any other buffer having a $pK_a$ in the pH range of from about 4 to about 8. The buffer concentration may be in the range of from about 0.01 M to about 1 M, and is preferably 0.1 M.

The aloesin obtained by the hydrolysis process described above may be used in topical skin compositions. The aloin may be used in various compositions for the human and veterinary markets.

EXAMPLES

In the examples, hydrochloric acid and sulphuric acid were used to demonstrate the ability of acids to hydrolyse aloeresin A to aloesin, and *Aspergillus oryzae* protease was used to demonstrate enzymatic hydrolysis of aloeresin A to aloesin.

A quantitative HPLC method was developed as an analytical tool to monitor the amount of aloeresin A, aloesin and p-coumaric acid during optimisation of the hydrolysis process described herein. Details of the tests and results are set out in the examples below.

Example 1

Acid Hydrolysis Using HCl and Acetone

Aloe sap containing aloeresin A (15%) was hydrolysed at 90° C. with 1.3 or 5 N HCl in the presence or absence of acetone over time. The acetone was used to increase the solubility of substrate in the aloe sap. Aliquots (20 μl) of the reaction were taken at timed intervals, and were added to 100 mM phosphate buffer, pH 7.2, containing 30% acetone. Analysis of samples was performed by HPLC, using established methods.

Results showed that the rate of hydrolysis was dependent on acid strength, and that between 40% and 80% conversion was achieved when 5 N HCl was used. The presence of 10% acetone improved hydrolysis slightly. The rate of aloeresin A disappearance was greater at higher acid strength. The results also showed that 90-95% aloeresin A had disappeared within 2 h at 3 to 5 N HCl.

Example 2

Acid Hydrolysis Using HCl or $H_2SO_4$ and Ethanol

Ethanol was used as an alternative to acetone. Aloe extract containing aloeresin A was hydrolysed at 90° C. with 1 N HCl or $H_2SO_4$ in the presence of 50% (v/v) ethanol over the times shown. The amount of aloe extract was varied from 10 to 50% (v/v). Aliquots (1 ml) of each reaction were taken at the indicated time intervals, and were added to 0.5 ml cold acetone. Analysis of samples was performed by HPLC, using established methods.

Mole balance closures between aloeresin A and aloesin were in the region of 80% after 4 h reaction (and were possibly higher within this period), using $H_2SO_4$ as the hydrolysing acid and an aloe sap concentration of 30%. Mole balance closures were about 10% higher when $H_2SO_4$ was used as the acid, but losses in mole balances were observed sooner compared to HCl.

Example 3

Enzymatic Hydrolysis Using *Aspergillus Oryzae* Protease

Variable conditions were tested so as to preliminary optimise the enzymatic hydrolysis or aloeresin A to aloesin in an aloe extract or pure aloeresin A. *Aspergillus oryzae* protease was selected as an example of a hydrolytic enzyme, and two *Aspergillus oryzae* proteases were tested, the one being PROTEASE M™ from Amano and the other being BIOPROTEASE P CONC™ from Quest International.

PROTEASE M™ Specifications:
  Origin: *Asp. oryzae* (Non-GMO)
  Diluent: Potato Dextrin (Non-GMO)
  Contents of diluent: Approx. 15%

BIOPROTEASE P CONC™ Specifications:
  minimum 400,000 HUT Protease u/gm
  Total Viable Count <50,000/gm
  Yeast & Moulds <200/gm
  *E. coli*: Absent in 25 gms
  *Salmonella*: Absent in 25 gms
  Meets all other international specifications (heavy metals, lead, arsenic, etc.) as set out by FCC & JECFA.

The following parameters were investigated on a small scale:

| | |
|---|---|
| Enzyme concentration: | 1 to 50 mgl enzyme |
| Aloe extract: | 15 μl to 200 μl per 3 ml |
| Buffer types: | Sodium phosphate, borate, or carbonate |
| Buffer concentrations: | 0.001 M to 1 M |
| pH: | 4 to 7 |
| Tween concentrations: | 0, 1 and 10% v/v |
| Acetone concentration: | 0 to 50% |

Typically at least 50% increase in aloesin concentration was obtained when using aloe sap as substrate.

Example 4

Enzymatic Hydrolysis Using *Aspergillus oryzae* Protease

Reactions were carried out on 3 mg pure (91%) aloeresin A per 1 ml reaction using PROTEASE M™ from Amano or BIOPROTEASE P CONC™ from Quest International as enzyme. The parameters investigated were:

| | |
|---|---|
| Enzyme concentration: | 2 and 20 mg |
| Buffer concentration: | 0.01 M sodium phosphate |
| pH: | 5.5 |

Reactions were carried out at 37° C. with agitation on a vibrating agitator, over 20 h. Complete conversion of aloeresin A to aloesin was accomplished.

For all the reactions, the whole reaction of 3 ml was submitted for analysis. The samples were made up to 25 ml with water:methanol:THF (20:40:40) and analysed on HPLC.

It was determined that the *Aspergillus oryzae* protease functions optimally at 37° C. The enzyme conversion of aloeresin A to aloesin and p-coumaric acid was optimised using the parameters described above, and conditions were found where aloeresin A is fully converted to aloesin and p-coumaric acid. After 4 h there was a 100% increase in the aloesin content and a 100% decrease in aloeresin A. The conversion was therefore complete with a mole balance of close to 100% when using pure aloeresin A as substrate.

Example 5

Large Scale Production of Aloesin

The reactions were carried out in a jacketed, stirred tank, glass-lined reactor. Aloe sap was hydrolysed using an equivalent mass of a 2 molar HCl solution under nitrogen. The reactor was heated to 90° C. and the temperature maintained for approximately 5.5 hours. The conversion of aloeresin obtained was ca. 94%, with an average selectivity to aloesin of ca. 30%.

At the end of the reaction, the reactor content was cooled to 70° C. by passing chilled water through the jacket. The system was neutralised using a 45% caustic solution (ca. 0.75 equivalents to the acid) to a pH of ca. 4.5.

The reactor was further cooled to 28° C., and the agitation stopped. The reaction mixture is allowed to separate into 2 phases. The aqueous phase (referred to as hydrolysate) settled to the bottom and top layer containing solids settled on top (referred to as the top layer). The hydrolysate was drained to a holding tank.

The top layer was aerated with nitrogen together with agitation prior to the addition of water. The reactor contents were then washed with an equivalent mass of water. The reactor was stirred at 25° C. for 30 minutes and then allowed to stand for an additional 30 minutes.

The separation of the mixture was carried out at 25° C., with the top layer remaining at the top. The aqueous phase was drained to the holding tank. The water wash was combined with the hydrolysate drained earlier. The total aloesin recovered from the post reaction stream was ca. 84%.

The remaining solids were removed from the reactor by dissolution in a 10% caustic solution. The wash solution is then drained and treated as waste.

The invention is not intended to be limited to the precise details as herein described. For example, the applicant envisages that other hydrolytic agents could also be used in the hydrolysis reaction, such as acids and enzymes which are chemical or biochemical equivalents of the tested acids or enzymes.

The invention claimed is:

1. A method of extracting aloesin from aloe bitters comprising:
   i.) subjecting aloe bitters obtained from an aloe plant to hydrolysis with an inorganic acid in a concentration of about 0.5N to about 10N, wherein said inorganic acid is selected from the group consisting of: hydrochloric acid, sulfuric acid, nitric acid and phosphoric acid, to provide hydrolyzed aloe bitters, and wherein said hydrolysis converts aloeresin A in the aloe bitters to aloesin and p-coumaric acid; and
   ii.) extracting the aloesin from the hydrolyzed aloe bitters.

2. The method of claim 1, wherein the aloe plant is *Aloe ferox*.

3. The method of claim 1, wherein the inorganic acid is in a concentration of about 2N to about 5N.

4. The method of claim 1, wherein said hydrolysis occurs in the presence of an organic solvent.

5. The method of claim 1, wherein the organic solvent is ethanol or acetone.

* * * * *